United States Patent
Crouse et al.

(10) Patent No.: US 11,714,040 B2
(45) Date of Patent: Aug. 1, 2023

(54) DETERMINING FLUID FLOW CHARACTERISTICS OF POROUS MEDIUMS

(71) Applicant: Dassault Systemes Simulia Corp., Johnston, RI (US)

(72) Inventors: Bernd Crouse, Berkeley, CA (US); David M. Freed, Brisbane, CA (US); Ashraful Islam, Daly City, CA (US)

(73) Assignee: Dassault Systemes Simulia Corp., Johnston, RI (US)

( * ) Notice: Subject to any disclaimer, the term of this patent is extended or adjusted under 35 U.S.C. 154(b) by 1224 days.

(21) Appl. No.: 16/243,285

(22) Filed: Jan. 9, 2019

(65) Prior Publication Data

US 2019/0212241 A1    Jul. 11, 2019

Related U.S. Application Data

(60) Provisional application No. 62/615,701, filed on Jan. 10, 2018.

(51) Int. Cl.
*G01N 13/00* (2006.01)
*G01N 15/08* (2006.01)
(Continued)

(52) U.S. Cl.
CPC ......... *G01N 13/00* (2013.01); *G01N 15/0826* (2013.01); *G01N 23/00* (2013.01);
(Continued)

(58) Field of Classification Search
CPC .... G01N 13/00; G01N 15/0826; G01N 23/00; G01N 23/02; G01N 23/04; G01N 23/046
See application file for complete search history.

(56) References Cited

U.S. PATENT DOCUMENTS 3,818,757 A    6/1974  Brown
4,498,134 A    2/1985  Hansen et al.
(Continued)

FOREIGN PATENT DOCUMENTS

CN    101556687          10/2009
CN    102174888 A    *   9/2011
(Continued)

OTHER PUBLICATIONS

Dixit, Ashok B., et al. "Pore-scale modeling of wettability effects and their influence on oil recovery." SPE Reservoir Evaluation & Engineering 2.01 (1999): 25-36. (Year: 1999).*
(Continued)

*Primary Examiner* — Peter J Macchiarolo
*Assistant Examiner* — Fatemeh Esfandiari Nia
(74) *Attorney, Agent, or Firm* — Fish & Richardson P.C.

(57) ABSTRACT

Techniques including methods, apparatus and computer program products are disclosed. These techniques include computer instructions that are encoded on computer storage media for determining wettability. The techniques use a numerical aging computation process to provide a representation of a wettability alteration of a physical rock sample in the presence of at least two fluids is disclosed. The techniques include retrieving a representation of a physical rock sample, the representation including pore space and grain space data corresponding to the physical rock sample, calculating local curvature for each surface in the pore space, determining from the calculated local curvature whether water-film breakage will occur, and classifying the wettability of the physical rock based on the determination of water-film breakage.

34 Claims, 5 Drawing Sheets

(51) Int. Cl.
  *G01N 33/24* (2006.01)
  *G06F 30/20* (2020.01)
  *G01N 23/00* (2006.01)
  *G01N 23/046* (2018.01)
  *G01N 23/04* (2018.01)
  *G01N 23/02* (2006.01)
  *G06F 30/28* (2020.01)
  *G06F 111/10* (2020.01)

(52) U.S. Cl.
  CPC .............. *G01N 23/02* (2013.01); *G01N 23/04* (2013.01); *G01N 23/046* (2013.01); *G01N 33/24* (2013.01); *G06F 30/20* (2020.01); *G06F 30/28* (2020.01); *G06F 2111/10* (2020.01)

(56) References Cited

U.S. PATENT DOCUMENTS

| | | |
|---|---|---|
| 4,507,726 A | 3/1985 | Grinberg et al. |
| 4,729,098 A | 3/1988 | Cline et al. |
| 4,809,202 A | 2/1989 | Wolfram |
| 4,831,519 A | 5/1989 | Morton |
| 4,860,245 A | 8/1989 | Kinoshita |
| 4,933,895 A | 6/1990 | Grinberg et al. |
| 4,969,116 A | 11/1990 | Wada et al. |
| 4,989,166 A | 1/1991 | Akasaka et al. |
| 5,038,302 A | 8/1991 | Kaufman |
| 5,159,690 A | 10/1992 | Margolus |
| 5,255,212 A | 10/1993 | Kondoh et al. |
| 5,361,385 A | 11/1994 | Bakalash |
| 5,377,129 A | 12/1994 | Molvig et al. |
| 5,408,638 A | 4/1995 | Sagawa et al. |
| 5,416,729 A | 5/1995 | Leon et al. |
| 5,424,963 A | 6/1995 | Turner et al. |
| 5,432,718 A | 7/1995 | Molvig et al. |
| 5,442,733 A | 8/1995 | Kaufman et al. |
| 5,548,694 A | 8/1996 | Frisken Gibson |
| 5,594,671 A | 1/1997 | Chen et al. |
| 5,605,517 A | 2/1997 | Sherman |
| 5,606,517 A | 2/1997 | Traub et al. |
| 5,640,335 A | 6/1997 | Molvig et al. |
| 5,848,260 A | 12/1998 | Chen et al. |
| 5,953,239 A | 9/1999 | Teixeira et al. |
| 6,318,156 B1 | 11/2001 | Dutton et al. |
| 6,516,080 B1 | 2/2003 | Nur |
| 6,915,245 B1 | 7/2005 | Hinton et al. |
| 6,928,399 B1 | 8/2005 | Watts et al. |
| 7,209,873 B1 | 4/2007 | Kliegel |
| 7,590,514 B1 | 9/2009 | Olovsson |
| 8,583,411 B2 | 11/2013 | Fung |
| 8,757,871 B2 | 6/2014 | Gruebele et al. |
| 9,058,446 B2 | 6/2015 | Lu et al. |
| 9,228,873 B2 | 1/2016 | Crouse et al. |
| 9,507,047 B1 | 11/2016 | Dvorkin et al. |
| 10,101,188 B2 | 10/2018 | Crouse et al. |
| 10,550,690 B2 | 2/2020 | Crouse et al. |
| 10,762,252 B2 | 9/2020 | Gopalakrishnan et al. |
| 11,118,449 B2 | 9/2021 | Crouse et al. |
| 2002/0173915 A1 | 11/2002 | Egermann et al. |
| 2005/0182603 A1 | 8/2005 | Freitas et al. |
| 2006/0132131 A1* | 6/2006 | Fleury .............. G01N 15/0826 324/303 |
| 2006/0277012 A1 | 12/2006 | Ricard et al. |
| 2007/0016389 A1 | 1/2007 | Ozgen |
| 2008/0044543 A1 | 2/2008 | McClements et al. |
| 2009/0070085 A1 | 3/2009 | Gullapalli et al. |
| 2010/0030534 A1 | 2/2010 | Reich et al. |
| 2010/0128932 A1 | 5/2010 | Dvorkin et al. |
| 2010/0156901 A1* | 6/2010 | Park ..................... G06T 15/205 345/420 |
| 2010/0312535 A1 | 12/2010 | Chen et al. |
| 2011/0184711 A1 | 7/2011 | Altman et al. |
| 2011/0313744 A1 | 12/2011 | Oury et al. |
| 2012/0179436 A1 | 7/2012 | Fung |
| 2012/0191432 A1 | 7/2012 | Khataniar et al. |
| 2012/0241149 A1* | 9/2012 | Chen ..................... G01V 3/32 324/303 |
| 2012/0310614 A1* | 12/2012 | Beattie ................ E21B 43/16 703/10 |
| 2013/0018641 A1 | 1/2013 | de Prisco et al. |
| 2013/0080128 A1 | 3/2013 | Yang et al. |
| 2013/0116997 A1 | 5/2013 | Sun et al. |
| 2013/0151221 A1 | 6/2013 | Chen et al. |
| 2013/0317791 A1 | 11/2013 | Danielson |
| 2014/0019053 A1 | 1/2014 | de Prisco |
| 2014/0067347 A1 | 3/2014 | Gurpinar et al. |
| 2014/0343858 A1* | 11/2014 | Crouse ................. G01V 99/00 702/13 |
| 2015/0048007 A1 | 2/2015 | Weerasooriya et al. |
| 2015/0051892 A1 | 2/2015 | Carvajal et al. |
| 2015/0059447 A1 | 3/2015 | Rickards |
| 2015/0066463 A1 | 3/2015 | Shetty et al. |
| 2015/0141303 A1 | 5/2015 | Harwell et al. |
| 2015/0142407 A1 | 5/2015 | Wakefield et al. |
| 2015/0149139 A1 | 5/2015 | Chavez et al. |
| 2016/0003010 A1 | 1/2016 | Fomel et al. |
| 2016/0188768 A1 | 6/2016 | Gopalakrishnan et al. |
| 2016/0209256 A1 | 7/2016 | Crouse et al. |
| 2016/0307359 A1 | 10/2016 | Desbrun et al. |
| 2017/0198573 A1* | 7/2017 | Kim ..................... E21B 43/26 |
| 2018/0329112 A1 | 1/2018 | Lee et al. |
| 2018/0120213 A1* | 5/2018 | Dyshlyuk .............. G01N 23/05 |
| 2018/0253514 A1* | 9/2018 | Bryant ................... G06F 30/20 |
| 2019/0050508 A1 | 2/2019 | Crouse et al. |
| 2019/0086250 A1 | 3/2019 | Crouse et al. |
| 2019/0154597 A1 | 5/2019 | Zhang |
| 2019/0186255 A1 | 6/2019 | Mustapha |
| 2019/0203593 A1* | 7/2019 | Fullmer ............... G01V 99/005 |
| 2019/0368344 A1 | 12/2019 | Crouse et al. |
| 2020/0063532 A1 | 2/2020 | Crouse et al. |
| 2021/0062638 A1 | 3/2021 | Crouse et al. |
| 2021/0406434 A1 | 12/2021 | Gopalakrishnan et al. |

FOREIGN PATENT DOCUMENTS

| | | |
|---|---|---|
| CN | 102245289 | 11/2011 |
| CN | 102472649 | 5/2012 |
| CN | 103698102 | 4/2014 |
| CN | 104067290 | 9/2014 |
| CN | 104334828 | 2/2015 |
| CN | 102383783 | 6/2015 |
| CN | 105580019 | 5/2016 |
| CN | 105910996 | 8/2016 |
| CN | 106233146 | 12/2016 |
| EP | 0228915 | 7/1987 |
| GB | 2066466 | 7/1981 |
| JP | 2011/191848 | 9/2011 |
| WO | WO 1991017204 | 11/1991 |
| WO | WO 1992001993 | 2/1992 |
| WO | WO99/34308 | 7/1999 |
| WO | WO2008021652 | 2/2008 |
| WO | WO2012/071090 | 5/2012 |
| WO | WO 2016/159807 | 10/2016 |
| WO | WO 2019097272 | 5/2019 |

OTHER PUBLICATIONS

Catala, et al. "Fluid Flow Fundamentals." Oilfield Review, 1996, pp. 61-64.
CN Office Action in Chinese Appln. No. 201580021949.2, dated Aug. 10, 2018, 103 pages (with English translation).
Hoshen & Kopelman, "Percolation and cluster distribution. I. Cluster multiple labeling technique and critical concentration algorithm," Physical Review B, 1976, 14:8:3438-3445.
PCT International Search Report and Written Opinion in International Appln. No. PCT/US2015/021075, dated Jul. 8, 2015; 10 pp.
PCT International Search Report and Written Opinion in International Appln. No. PCT/US2019/013079, dated Apr. 1, 2019, 12 pages.
Pepiot et al., "Numerical analysis of the dynamics of two- and

(56) References Cited

OTHER PUBLICATIONS three-dimensional fluidized bed reactors using an Euler-Lagrange approach," Powder Technology, 2011, 220 (2012) 104-121.
Prodanovic et al, "Investigating Matrix-Fracture Transfer via a Level Set Method for Drainage and Imbibition"; SPE Journal, vol. 15, No. 01; Mar. 1, 2010; 17 pages.
Supplemental European Search Report; EP 15 76 4161; dated Nov. 10, 2017; 9 pages.
Yiotis et al., "Blob population dynamics during immiscible two-phase flows in reconstructed prorous media"; Physical Review, 2013, E 87, 033001, 12 pp.
EP Extended European Search Report in EP Appln. No. 19738994. 3, dated Feb. 2, 2021, 12 pages.
EP Extended European Search Report in EP Appln. No. 20194619. 1, dated Jan. 28, 2021, 6 pages.
Man et al.. "Pore Network Modelling of Electrical Resistivity and Capillary Pressure Characteristics". Transport in Porous Media, Dec. 2000, 41(3):263-285.
Mohammadmoradi et al., "Petrophysical Characterization of Porous Media Starting from Micro-Tomographic Images", Advances in Water Resources, May 2016, 35 pages.
Moteaileh et al., "Unified Model of Drainage and Imbibition in 3D Fractionally Wet Porous Media" Transport in Porous Media, Jul. 2013, 99(3):581-611.
Pereira, "Fluid Flow, Relative Permeabilities and Capillary Pressure Curves Through Heterogeneous Porous Media," Applied Mathematical Modelling, May 31, 2019, vol. 75, p. 481-493.
Bao et al., "Lattice Boltzmann method for fluid simulations," Department of Mathematics, Courant Institute of Mathematical Sciences, New York University, Apr. 14, 2011, 44:1-16.
Chatterjee et al., "A hybrid lattice Boltzmann model for solid-liquid phase transition in presence of fluid flow," Physics Letters A, Mar. 6, 2006, 351(4-5):359-367.
Chen & Ohashi, "The foundation and its application of the lattice Boltzmann method," Simulation, Nippon-Steel Technical Information Center, Ltd., Sep. 15, 1998, 17(3): 43-49 (with abstract).
Chen et al., "Lattice Boltzmann method for fluid flows," Annual review of fluid mechanics, Jan. 1998, 30(1):329-64.
CN Office Action in Chinese Appln. No. 201480049496.X; dated Dec. 18, 2017; 18 pages (with English translation).
EP Extended European Search Report in EP Appln. No. 18744797. 4, dated Dec. 5, 2019, 10 pages.
EP Office Action in European Appln. No. 15764161.4-1001, dated Apr. 15, 2019, 8 pages.
EP Office Action in European Appln. No. 19192927.2 dated Jan. 7, 2020, 9 pages.
EP Supplemental European Search Report and Written Opinion, in European Appln. No. 14797363, dated Apr. 18, 2017, 11 pages.
EP Supplemental European Search Report in European Appln. No. 14832274.6, dated Apr. 3, 2017, 7 pages.
EP Supplemental European Search Report in European Appln. No. 18744797.4, dated Dec. 5, 2019, 39 pages.
EPO Extended European Search Report in European Appln. No. 19192927.2, dated Jan. 7, 2020, 9 pages.
Hamedi et al., "Pore-scale investigation of phase distribution and residual-oil development during secondary and tertiary solvent injection," SPE Reservoir Evaluation & Engineering. Feb. 1, 2015, 18(01):39-52.
Han et al., "Modelling of thermal contact resistance within the framework of the thermal lattice Boltzmann method," International Journal of Thermal Sciences, Oct. 1, 2008, 47(10):1276-1283.
Healy et al., "Status of Miscible Flooding Technology," 14th World Petroleum Congress, Jan. 1, 1994, 407-409.
Huang et al.; "Shan-and-Chen Type Multiphase Lattice Boltzmann Study of Viscous Coupling Effects for Two-Phase Flow in Porour Media," International Journal for Numerical Methods in Fluids, Sep. 30, 2009; 61(3):341-354.
JP Office Action in Japanese Appln. No. 2016-507600, dated Jul. 10, 2018, 23 pages (with English translation).
Karsch, "Lattice simulations of the thermodynamics of strongly interacting elementary particles and the exploration of new phases of matter in relativistic heavy ion collisions," InJournal of Physics: Conference Series 2006 , 46(1):122-131.
Ladd et al., "Lattice-Boltzmann simulations of particle-fluid suspensions," Journal of statistical physics, Sep. 1, 2001, 104(5-6):1191-251.
Lee et al. "A stable discretization of the lattice Boltzmann equation for simulation of incompressible two-phase flows at high density ratio," Journal of Computational Physics, Jun. 10, 2005, 206(1):16-47.
Notification of Reasons for Rejection with English Translation; JP Appln. No. 2016-514084; dated Jun. 21, 2018, 6 pages.
PCT International Search Report and Written Opinion, in International Appln. No. PCT/US2014/038143, dated Sep. 10, 2014, 9 pages.
PCT International Search Report and Written Opinion, in International Appln. No. PCT/US2018/015408, dated Mar. 12, 2018, 6 pages.
Petkov et al., "Efficient LBM visual simulation on face-centered cubic lattices," IEEE Transactions on Visualization and Computer Graphics, Feb. 27, 2009, 15(5):802-14.
petrowiki.org/Miscible_flooding [online] "Miscible flooding" Aug. 19, 2013, retrieved on Oct. 10, 2019, retrieved from URL <https://petrowiki.org/Miscible_flooding>, 9 pages.
Raabe, "Overview of the lattice Boltzmann method for nano-and microscale fluid dynamics in materials science and engineering," Modelling and Simulation in Materials Science and Engineering, Sep. 16, 2004, 12(6):R13-R46.
Ramstad et al., "Simulation of two-phase flow in reservoir rocks using a lattice Boltzmann method," Spe Journal, Dec. 1, 2010, 15(04):917-27.
Sohrabi et al., "Novel Insights into the Pore-scale Mechanisms of Enhanced Oil Recovery by CO2 Injection," 74th EAGE Conference and Exhibition, Jun. 4, 2012, 154529:1-14.
Sohrabi et al., "Visualisation of residual oil recovery by near-miscible gas and SWAG injection using high-pressure micromodels," Transport in Porous Media, Sep. 1, 2008, 74(2):239-57.
Tsuji et al., "Characterization of immiscible fluid displacement processes with various capillary numbers and viscosity ratios in 3D natural sandstone," Advances in Water Resources, Sep. 1, 2016, 95:3-15.
Van Den Pijl, "Computation of bubbly flows with a mass-conserving level-set method," Dissertation at Delft University of Technology, Nov. 22, 2005, 139 pages.
Xu et al., "Continuous vs Discontinuous Capillary Desaturation and Implications for IOR/EOR," InPaper SCA2018-066 presented at at the International Symposium of the Society of Core Analysts held in Trondheim, Norway, Aug. 2018, 1-10.
"*A Pore-Leval Scenario for the Development of Mixed-Wettability in Oil Reservoirs,* " Kovscek et al., Earth Science Division of Lawrence Berkeley Laboratory and Department of Chemical Engineering, prepared for U.S. Department of Energy, Sep. 1992, p. 1-58.
"*Optimizing 3D Triangulations Using Discrete Curvature Analysis,* " Dyn et al., Mathematical Methods for Curves and Surfaces: Oslo 2000, pp. 135-146.
U.S. Appl. No. 07/555,754, filed Jul. 12, 1990, Molvig.
U.S. Appl. No. 07/812,881, filed Dec. 20, 1991, Molvig.
Bryant et al., "Prediction of relative permeability in simple porous media" Physical Review A vol. 46, No. 4 Aug. 15, 1992) (Year: 1992).
Burges et al., "Buoyant Mixtures of Cellular Automation Gases," Complex Systems, 1:31-50 (1987).
Chen et al., "Lattice Boltzmann Model for Stimulation of Magnetohydordynamicis," Physical Review Letters, vol. 67,No. 27 (Dec. 1991), pp. 3776-3779.
Chopard et al., Cellular Automata Model for Heat Conduction in a Fluid, Physics Letters A, vol. 126, Nos. 8, 9, pp. 476-480 (Jan. 1988).
Clougueur et al., "RAPI, A Cellular Automaton Machine for Fluid Dynamics," Complex Systems, pp. 585-597 (1987).

(56) References Cited

OTHER PUBLICATIONS

Demianov et al., "Density Functional Modelling in Multiphase Compositional Hydrodyanmics" Canadian J. Chem. Engine., Apr. 2011. 89:206-26.
D'Humieres et al., "2-D and 3-D Hydrodynamics on Lattice Gases," Fruhjahrstagung der Schweiz. Physikalischen Gesellschaft, vol. 59 (1986).
D'Humieres et al., "Lattice Gas Models for 3D Hydrodynamics," 2 (4), pp. 291-297 (1986).
D'Humieres et al., Numerial Simulations of Hydrodynamics with Lattice Gas Automata in Two Dimensions, Complex Systems 1:599-632 (1987).
Fredkin et al., "Conservative Logic." International Journal of Theoretical Pysics, vol. 21, Nos. 3/4, pp. 219-253 (1982).
Frisch et al., "Lattice Gas Hydrodynamics in Two and Three Dimensions." Complex Systems 1:649-707 (1987).
Frisch et al., "Lattice-Gas Automata for the Navier-Stokes Equation," Physical Review Letters, vol. 56, No. 14, pp. 1505-1508 (Apr. 1986).
Ginzburg et al., "Analysis and improvement of Brinkman lattice Boltzmann schemes: Bulk, boundary, interface. Similarity and distinctness with finite elements in heterogeneous porous media" Physical Review, 2015, 91:023307-1-32.
Google Search Results, Jun. 28, 2021, 1 pp. (Year: 2021.
Hardy et al., "Molecular Dynamics of a Classical Lattice Gas: Transport Properties and Time Correlation Functions." Physical Review A, vol. 13, No. 5, pp. 1949-1961 (May 1976).
Hasslacher, Discrete Fluids: Part I: Background for Lattice Gas Automata, Los Alamos Science Special Issue, pp. 175-217 (1987).
Henon, "Isometric Collision Rules for the Four-Dimensional FCHC Lattice Gas," Complex Systems 1:475-494 (1987).
Jiang et al, "Estimation of three-phase relative permeability by simulating fluid dynamics directly on rock-microstructure images," Jan. 5, 2017, 22 pages.
Kadanoff et al., "Transport Coefficients Near the Critical Point: A Master Equation Approach," 165 Phys. Review 310 (1968).
Kadanoff, "On Two Levels" Physics Today (Sep. 1986).
Kaufman et al. "Volume Graphics." IEEE, Jul. 1993, pp. 51-64.
Klein, "Negative Absolute Temperatures." Physical Review, vol. 104, No. 3, p. 589 (Nov. 1956).
Krummel et al. "Visualizing Multiphase Flow and Trapped Fluid Configurations in a Model Three-Dimensional Porous Medium" (Year: 2013).
Lenormand et al., "Physics of Blob Displacement in a Two-Dimensional Porous Medium," Mar. 1988, SPE Formation Evaluation, pp. 271-275.
Li et al. "GPU-based numerical simulation of multi-phase flow in porous media using multiplerelaxation-time lattice Boltzmann method" (Year: 2013).
Li et al., "Upscaled Lattice Boltzmann Method for Simulations of Flows in Heterogeneous Porous Media," Geofluids, Feb. 2017, 2017:1-12.
Lin et al., "Plasma Simulation Using the Massively Parallel Processor," NASA CP-2478, pp. 185-191 (Jul. 1987).
Margolus et al., "Cellular-Automata Supercomputers for Fluid-Dynamics Modeling." Physical Review Letters, vol. 56, No. 16, pp. 1694-1696 (Apr. 1986).
Martys et al., "Multiscale modeling of fluid transport in heterogeneous materials using discrete Boltzmann methods," Materials and Structures, Dec. 2002, 35:650-9.
Mohanty et al., Physics of Oil Entrapment in Water-Wet Rock, Feb. 1987, SPE Reservoir Engineering, pp. 113-128 (Year: 1987).
Molvig et al., "Fluid CAD That Challenges Computational Fluid Dynamics," Machine Design, Dec. 1994, 66(23):96-8.
Molvig et al., "Multi-species Lattice-Gas Automata for Realistic Fluid Dynamics," Springer Proceedings in Physics, vol. 46, pp. 206-231 (1990) (abstract only).
Molvig et al., "Removing the Discreteness Artifacts in 3D Lattice-Gas Fluids", Proceedings of the Workshop on Discrete Kinetic Theory, Lattice Gas Dynamics, and Foundations of Hydrodynamics, World Scientific Publishing Co., Pte., Ltd., Singapore (1989).
One Petro Search Results, Jan. 26, 2021, 11 pp. (Year: 2021).
Perez et al., "OUPPI-1, Asimd Computer Using Integrated Parallel Processors." Proc. of Compar Conf. Papers Plenary Sess. and Stream A Manchester, Sep. 12-16, 1988, British Comp. Soc. Parallel Proc. Spec. Group GB.
Prodanovic et al., "Physics-Driven Interface Modeling for Drainage and Imbibition in Fractures," Sep. 2009 SPE Journal, pp. 532-542 (Year: 2009).
Qian et al., "Lattice BGK Models for Navier-Stokes Equation." Europhysics Letters, 17(6):479-484 (1992).
Ramsey, "Thermodynamics and Statistical Mechanics at Negative Absolute Temperatures." Physical Review, vol. 103, No. 1, pp. 20-28 (Jul. 1956).
Ramstad et al., "Relative Permeability Calculations from Two-Phase Flow Simulations Directly on Digital Images of Porous Rocks" Transp Porous Med (2012) 94:487-504 (Year: 2012).
Rivet, "Three-Dimensional Lattice Gas Hydrodynamical Simulations: First Results." C.R. Acad. Sci. Paris, t. 305, Series II, pp. 751-756 (1987).
Rosenblum, "Photorealistic Terrain Imaging and Flight Simulation," IEEE, 1994 pp. 10-12.
Sheng et al., "Numerical Prediction of Relative Permeability from MicroCT Images: Comparison of Steady-State versus Displacement Methods," Oct. 30-Nov. 2, 2011, SPE Annual Technical Conference and Exhibition, Denver, Colorado, 16 pages.
Suhrer et al., "Upscaling Method for Obtaining Primary Drainage Capillary Pressure andResistivity Index with Digital Rock Physics," IPTC-20035-ABSTRACT, 2020, 13 pages.
Teixeira, "Continuum Limit of Lattice Gas Fluid Dynamics." B.A. Sc. Engineering Science University of Toronto (1988).
Toffoli, "Cellular Automata as an Alternative to (Rather Than an Approximation of) Differentiation Equation in Modeling Physics." Physica 10D: 117-127 (1984).
Tucker, "Cellular Automata Machine: The Ultimate Parallel Computer," High Technology, pp. 85-87 (Jun. 1984).
Vichniac, "Cellular-Automata Fluids." Instabilities and Nonequilibrium Structures II, pp. 97-116 (1989).
Vichniac, "Stimulating Physics with Cellular Automata." Physica, 10D:96-110, 1984 (abstract only).
Wijk et al., "Three Ways to Show 3D Fluid Flow" IEEE Computer Graphics and Applications, Sep. 1994, 14(5):33-9.
Wolfram, "Cellular Automation Fluids 1: Basic Theory," J. Stat. Phys., vol. 45, Nos. 3/4, pp. 471-526 (1986).
Zhang et al., "Single Component, Multiphase Fluids Flow Simulation in Porous Media with Lattice Boltzmann Method" 2012 Fourth International Conference on Computational and Information Sciences (Year: 2012).
Zhu et al., "Extending a Gray Lattice Boltzmann Model for Simulating Fluid Flow in Multi-Scale Porous Media," Sci. Rep., Apr. 2018, 8(5826):1-19.
PCT International Preliminary Report on Patentability in International Appln. No. PCT/US2019/013079, dated Jul. 14, 2020, 10 pages.

* cited by examiner

DETERMINING FLUID FLOW CHARACTERISTICS OF POROUS MEDIUMS

CROSS-REFERENCE TO RELATED APPLICATION

This application claims the benefit of U.S. Provisional Application No. 62/615,701, filed Jan. 10, 2018, entitled "Digital Rock Procedures for Determining Wettability" which is incorporated herein by reference.

BACKGROUND

Two-phase relative permeability describes how easily one fluid can be moved through a porous medium in the presence of another fluid. It is an important characteristic of hydrocarbon reservoir rocks and a crucial input to oil and gas reservoir modeling and simulation activities.

The term "wettability" is used as measure a fluid's tendency to stick to (or wet) surfaces compared to a second fluid in the same pore space that is the tendency of one fluid to spread on or adhere to a solid surface in the presence of other immiscible fluids. In the petroleum context, wettability is the tendency of a reservoir rock surface to preferentially contact a particular fluid in a multiphase or two-phase fluid system.

Relative permeability, and multi-phase flow through porous media in general, is dependent on various characteristics of the fluid-fluid-rock system, including rock surface properties, physical properties of each fluid, and flow conditions. One flow characteristic is the non-dimensional "Capillary number" (Ca) that represents the ratio of viscous forces to capillary forces. "Capillary number" (Ca) is usually defined as the superficial fluid velocity times the viscosity of a reference fluid divided by the fluid-fluid interfacial tension. Another characteristic is "wettability", which represents a preference of a rock surface for one fluid over another one, and is manifested as a measurable property known as contact angle. Wettability is often classified as water-wet (average contact angle 0-90 degrees), neutral-wet (~90 degrees), oil-wet (90-180 degrees), or some variation thereof such as strongly water-wet or weakly oil-wet.

Wettability has a strong influence on multi-phase flow behavior in porous material, such as oil and water, oil and gas, or water and gas flowing through reservoir rock. Reservoir rocks (unlike man-made materials) tend to have spatially varying wettability, i.e., the contact angle varies from location to location on the surfaces within the pore space of a rock. The contact angle distribution is a result of the mineral composition and the geological history of a hydrocarbon-bearing rock as well as surface texture, chemical composition of fluids (e.g., water, oil) in contact with the rock, etc. Prior to contact with oil, rocks are almost always naturally water-wet; as oil invades the pore-space over geologic time, the initial water-wet character may be altered in certain locations due to adhesion of substances within the oil phase. Mechanisms of wettability alteration depend on various local system properties such as pressure, temperature, mineral type, and fluid composition.

When rock samples are extracted from oil/gas reservoirs during the drilling process, they are often contaminated with mud and other fluids and chemicals. When those rock samples are subjected to laboratory experiments to obtain two-phase relative permeability curves or capillary pressure curves, a common lab test procedure is to first clean the rock and then attempt to restore the rock's natural (pre-extraction) wettability. This process of attempting to reestablish a fluid phase distribution and wettability distribution (e.g., contact angles) representative of the subsurface reservoir conditions is referred to as "aging." A typical aging procedure would involve cleaning the rock sample of contaminants and treating the rock sample with chemicals that induce a water-wet condition. The sample is next saturated with brine, and in a procedure referred to as "drainage", oil is pushed in (hence brine is pushed out) using estimated reservoir conditions of temperature and pressure. This system is then "aged" for a period of time, e.g. 4 weeks, allowing wettability alteration to occur, presumably in a fashion similar enough to what had occurred in the real subsurface rock formation so that a realistic wetting condition is restored.

SUMMARY

In one aspect, a computer implemented method for determining a wettability alteration of a physical rock sample in the presence of at least two fluids includes retrieving by a computing system a representation of a physical rock sample, the representation including pore space and grain space data corresponding to the physical rock sample, calculating by the computing system, local curvature for a surface location in the pore space, and classifying by the computer system wettability of the surface location corresponding to the physical rock based on the determination of local curvature.

The following are some of the additional features within this aspect. Calculating local curvature includes calculating by the computing system, local capillary pressure and local disjoining pressure of the surface locations in the pore space, and the method further includes determining from the calculated local curvature whether water-film breakage will occur; for some of the surface locations, determine whether water-film breakage will occur by comparing the capillary pressure to the sum of local curvature-based pressure and local disjoining pressure; and for at least some of the surface locations with water-film breakage, determine the degree of wettability alteration based on local surface properties, local fluid chemical composition, and aging time.

Producing further includes assigning input parameters needed for wettability simulation to the computer simulation environment. The representation of the rock sample is modeled as a triangulated mesh and fluid is represented by voxels with voxels assigned attributes. The voxels can be cut to conform the fluid to the triangulated mesh. The method further includes performing a drainage simulation to establish a fluid phase distribution according to user-specified conditions. The user-specified conditions are selected from the group consisting of representative of laboratory and reservoir conditions. Performing drainage simulation further includes simulating drainage using a fluid computational technique to establish fluid phase distribution for user-specified conditions through the rock sample representation. Performing drainage simulation further includes performing a local curvature calculation at each surface in the rock sample representation, and applying results of the local curvature calculation to calculate the local capillary pressure at every surface location.

After a performing an iteration of determining the numerical representation of wettability alteration, the method further includes allowing the fluid phases to redistribute due to the modified surface wettability and repeating determination the numerical representation of wettability alteration. The provides a numerical prediction of surface wettability alteration and resulting spatial distribution of wettability in the form of the calculated contact angle at each surface location. A discrete surface element and one or more fluid elements are in communication, and local wettability determinations are made that depend on the local properties of mineral type, fluid properties, fluid composition, capillary pressure, and disjoining pressure. The wettability alteration is iteratively performed followed by fluid phase redistribution, with the wettability alteration repeated until the computing system detects a convergence measured by a subsequent repetition not significantly changing values of determined contact angles.

Other aspects include computer program products tangibly stored on non-transitory computer readable media and computation systems such as computer systems, computer servers.

One or more of the above aspects may provide one or more of the following advantages. Wettability has a strong influence on multi-phase flow behavior in porous material, such as oil and water, oil and gas, or water and gas flowing through reservoir rock, reservoir rocks can be extracted from oil/gas reservoirs during the drilling process cleaned to measure physical, chemical and geometric properties that are modeled. The modeled rock samples undergo simulated aging and wettability alterations rather than subjecting the samples to the conventional laboratory procedures to obtain two-phase relative permeability curves or capillary pressure curves. The disclosed process of computational "aging" and "wettability alterations" can be performed in a much shorter period of time in comparison to the "aging" times in, e.g. 4 weeks, for the physical laboratory approaches mentioned above.

Other features and advantages of the invention will become apparent from the following description, and from the claims.

DETAILED DESCRIPTION

Figure 1:
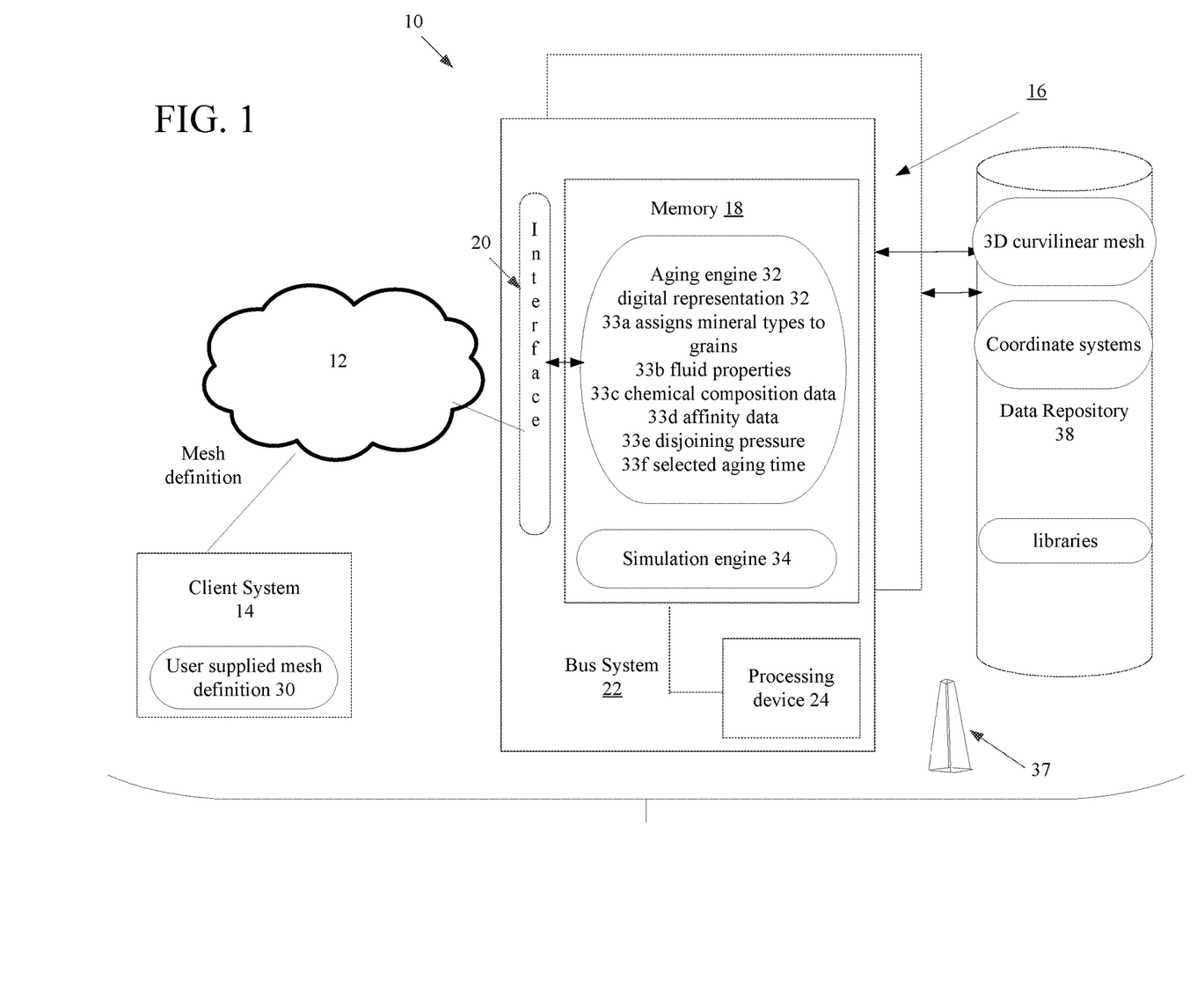
FIG. 1 depicts a system for simulation representation of wettability alteration.

Referring to FIG. 1, a system 10 for simulating to numerically simulate the wettability restoration or "aging" process representative of the subsurface reservoir conditions, i.e., "numerical aging" is shown. The system 10 in this implementation is based on a client-server or cloud based architecture and includes a server system 12 implemented as a massively parallel computing system 12 (stand alone or cloud-based) and a client system 14. The server system 12 includes memory 18, a bus system 11, interfaces 20 (e.g., user interfaces/network interfaces/display or monitor interfaces, etc.) and a processing device 24. In memory 18 are a numerical aging engine 32 that operates on a digital representation of a physical rock sample that digitally represents a pore space and grain space of the digital representation of the physical material, e. g., a physical rock sample (digital rock sample). Also in memory is a simulation engine 34 that simulates wettability alteration.

In some embodiments, simulating multi-phase flow behavior occurs through a reservoir rock adjacent a gas or oil well (e.g., drilling rig 37). Determining the multi-phase flow behavior comprises determining the wettability alteration of the physical rock sample.

The digital representation of the physical rock sample can be a third party application that is executed on a different system than server 12. The system 10 merely requires the digital representation of a physical rock sample 32' to have the numerical aging engine digitally prepare the digital representation of a physical rock sample. One approach to providing the digital representation 32' of the rock sample is to obtain the representation 32', for example, from a 3D image generated from a micro CT scan of the rock sample.

The memory 18 also stores parameters used by the engine 32, such as grain surface properties obtained by assigning mineral types 33a to the grains to determine the surface properties for each of those mineral types, and surface texture and roughness properties. The memory 18 also stores parameters such as fluid properties 33b, e.g., fluid density and viscosity of each expected fluid, (e.g., two or more of water, gas, oil) and fluid-fluid interfacial tension properties. The memory 18 also stores parameters such as chemical composition data 33c of the fluids and affinity data 33d of the fluid components for the particular mineral types. The memory 18 also stores disjoining pressure 33e for each mineral type in combination with the fluids, and a selected 33f aging time used by the aging engine 32. In addition, reservoir pressure and temperature data are also stored. The mineral types evaluated can be those found or expected at the actual site of the reservoir.

The simulation engine 34 includes a module 34a to set up the rock sample simulation environment, a module 34b to perform a drainage simulation, and a module 34c to calculate local curvature of surfaces in the pore space. The system 10 accesses a data repository 38 that stores 2D and/or 3D meshes, coordinate systems, and libraries that can be used for drainage simulations using any well-known computational technique such as computational fluid dynamics or the so called Lattice Boltzmann method.

Figure 2:
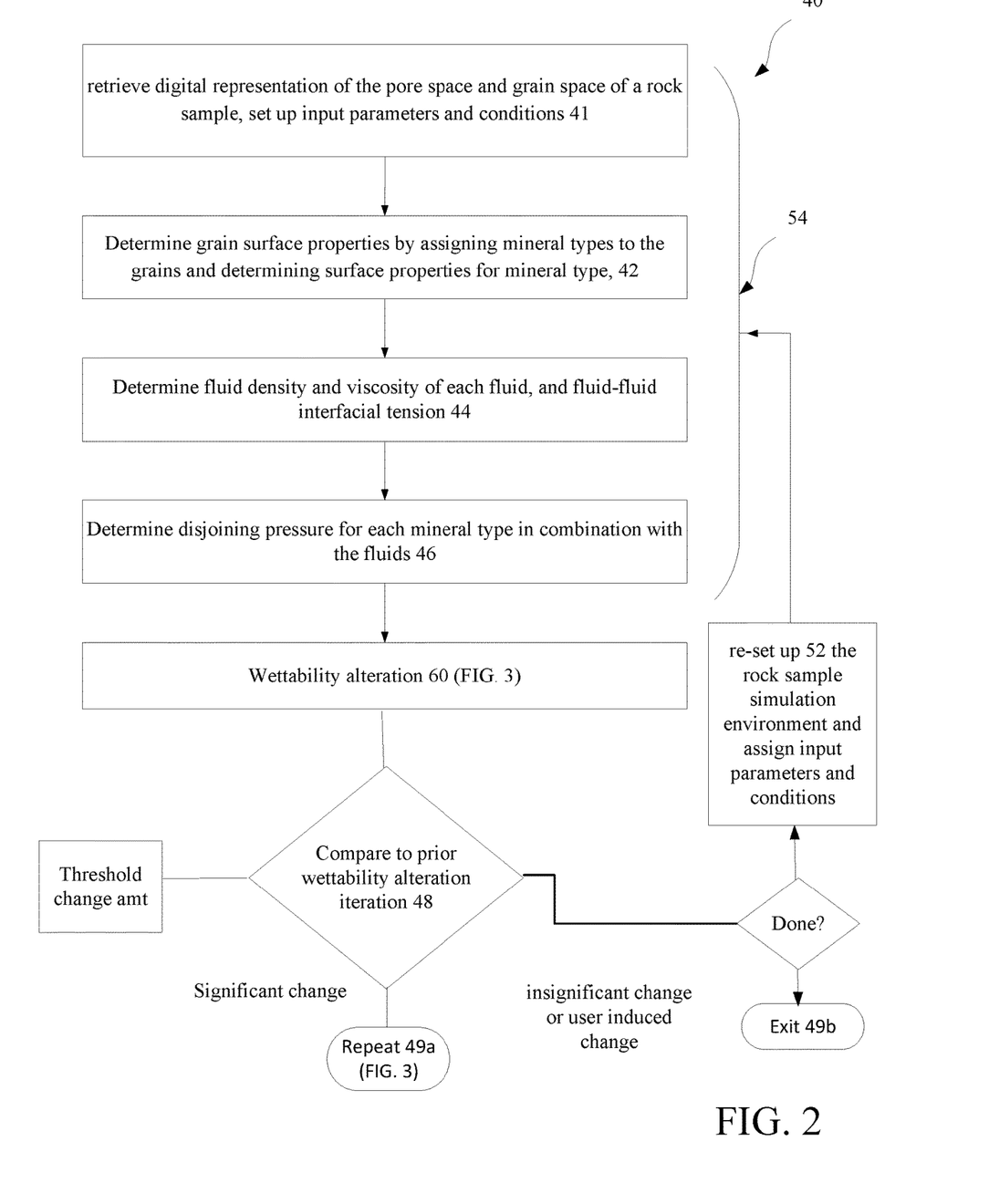
FIG. 2 depicts a flow chart showing operations for numerical aging.
Figure 3:
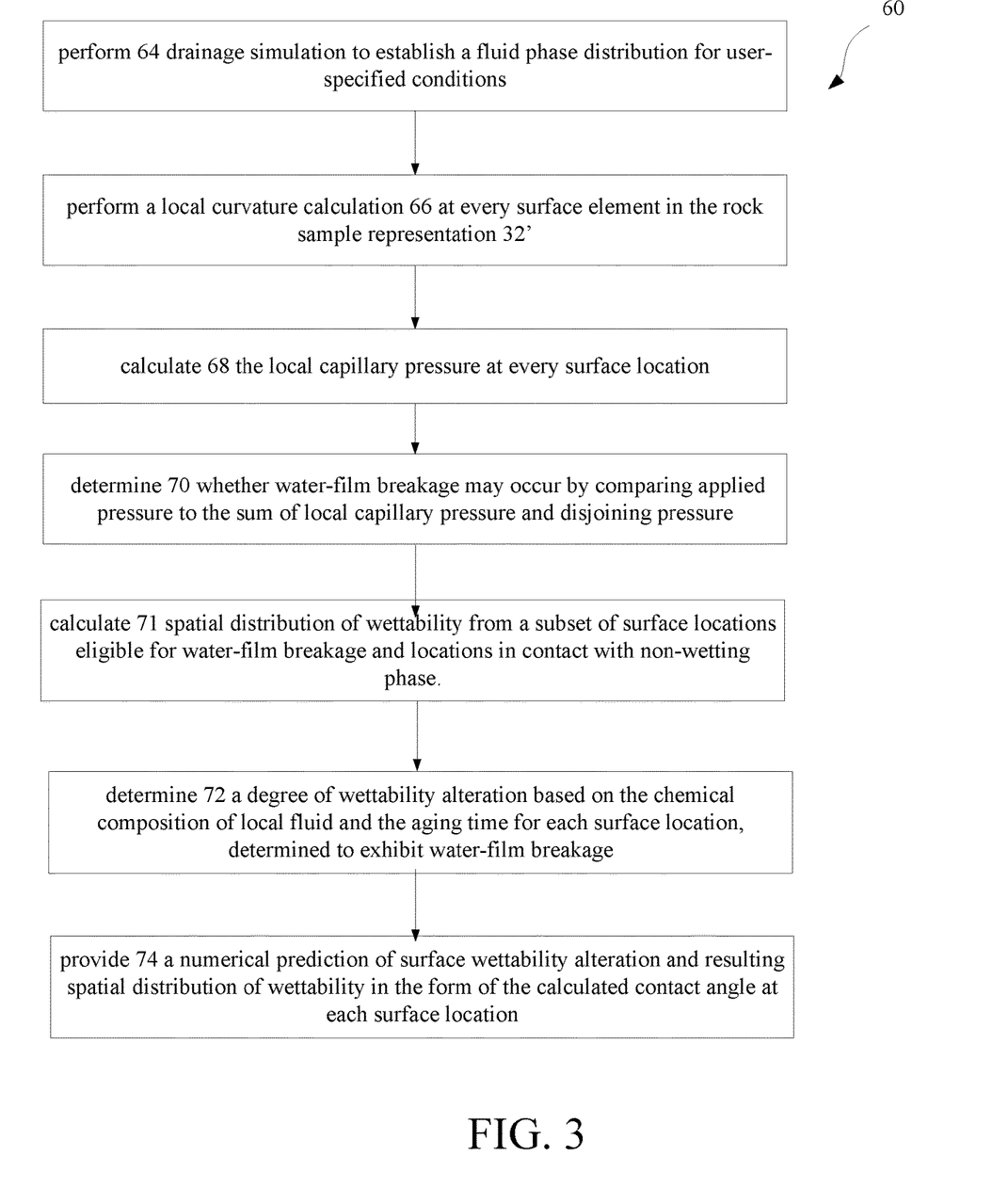
FIG. 3 depicts a flow chart showing operations for representation of wettability alteration simulations.

Referring now to FIG. 2, a process 40 for numerical aging retrieves 41 the digital representation of the pore space and grain space of a rock sample sets up input parameters and conditions, e.g., initial, and boundary conditions, determines 42 grain surface properties by assigning mineral types to the grains and determining surface properties for mineral type, determines 44 fluid density and viscosity of each fluid, and fluid-fluid interfacial tension determines 46 disjoining pressure for each mineral type in combination with the fluids and ages the digital representation of the rock for a time interval by performing a wettability alteration 60 (FIG. 3). Subsequent to an iteration of the wettability alteration process 60, the process 40 determines an amount of change 48 of the, e.g., local curvature, contact angle, etc., from a prior iteration of the wettability alteration process 60, and compares the amount to a threshold change amount. Grain surface properties include surface texture, more commonly referred to as surface "roughness" properties that will have an effect on contact angle.

If the change is significant the process 60 repeats 49a using a subsequent drainage simulation under specified conditions (FIG. 3). If the change is insignificant the process 40 can exit 49b or set up 52 a subsequent iteration of the rock sample simulation environment assigning a subsequent set of input parameters. The subsequent iteration 52 of the rock sample simulation can be used to change any of the elements of FIG. 2, as illustrated by the bracket 54.

The term "wettability" is used as measure a fluid's tendency to stick to (or wet) surfaces compared to a second fluid. That is "wettability" is the tendency of one fluid to spread on or adhere to a solid surface in the presence of other immiscible fluids. In the petroleum context, wettability is the tendency of a reservoir rock surface to preferentially contact a particular fluid in a multiphase or two-phase fluid system. Wettability can be influenced by an amount penetration of one fluid through another fluid, so as to cause a film breakage (i.e., the breakdown of the ability of a film of the first fluid to protect a surface from the second fluid. The wettability alteration process discussed below is used to simulate the effect that one fluid has on another fluid over time increments and surface and/or pore surface increments.

Referring now to FIG. 3, a process 60 for simulating wettability alteration is shown. In this example, the process 60 sets up 62 the rock sample simulation environment and assigns input parameters as specified above. The rock sample simulation environment includes the digital representation 32' of the pore space and grain space of the rock sample represented in the memory as a set of nodes 32" that have associated therewith the assigned input parameters as needed for wettability simulation.

For example, the 3D image generated from a micro CT scan of the rock sample can be digitized and represented, e.g., as a graph structure in memory with the graph having nodes and leafs, e.g., on a pixel by pixel basis (or groups of pixels). Pores can be identified by relative contrast levels. The process may execute a best-path algorithm (for example, using the Dijkstra method) to find pore lengths. The best path may be considered the centerline for the pore. The process identifies a contrast level for each node/pixel on the centerlines and can filter high-frequency values of contrast level, the process may use other filtering and/or spatial smoothing techniques to filter high frequency values. The nodes can be annotated with input parameters needed for wettability simulation.

Other representation can be of voxels. For example, prior to the simulation, the rock simulation environment is modeled as a collection of voxels. A triangulated mesh image process (a type of polygon mesh used in computer graphics, which comprises a set of triangles connected by common edges or corners) and segmentation mesh construction can be used to represent the surface of the rock sample in the simulation environment, and fluid is represented by voxels that are allowed to be 'cut.' The voxels are cut to conform the voxels to the mesh. Each voxel cell is assigned attributes.

The process 60 performs a drainage simulation 64 to establish a fluid phase distribution for user-specified conditions (that can be representative of either laboratory and/or reservoir conditions), such conditions including pressure and temperature of the reservoir. The drainage simulation is iteratively perform on portions of the rock sample. Most often, the rock sample is initially uniformly water-wet, but other initial wettability definitions are possible. The process can access, e.g., 3D meshes and coordinate systems, which together with libraries are used to simulate drainage using any well-known computational technique such as computational fluid dynamics or the so called Lattice Boltzmann method. The simulation will establish fluid phase distribution for user-specified conditions through the rock sample representation 32'.

The process 60 performs a local curvature calculation 66 at every surface in the rock sample representation 32', e.g., exterior surfaces and interior pore surfaces. From the local curvature calculations, the process 60 calculates 68 local capillary pressure at each surface location and determines 70 whether water-film breakage may occur at the surface, by comparing local capillary pressure to the sum of geometric induced, curvature-based pressure and disjoining pressure. For very small pores, the disjoining pressure effect due to a very large curvature will outweigh the effect of a material based disjoining pressure. In that case, only the curvature of the pore space is of significance. This scenario may happen in clay or in shale type formations.

The curvature of the surface of the rock is calculated using differential geometry. One particular tool is "VTK" (Visualization Toolkit an open-source, freely available software system for 3D computer graphics.) Other tools, etc. could be used as well as other techniques could be used. Differential geometry is also discussed in Optimizing 3D Triangulations Using Discrete Curvature Analysis Nira Dyn, et al. (2001) (obtained from https://www.inf.usi.ch/hormann/papers/Dyn.2001.OTU.pdf) the entire contents of which are incorporated herein by reference. The process 60 calculates 71 a spatial distribution of wettability by taking a subset of surface locations eligible for water-film breakage and locations in contact with the non-wetting phase which is obtained after drainage simulation and determines 72, a degree of wettability alteration based on the chemical composition of the local fluid and the aging time, with longer aging times likely resulting in more oil-wet (larger) contact angles compared to shorter aging times. The process can then classify the wettability as water-wet (average contact angle 0-90 degrees), neutral-wet (~90 degrees), oil-wet (90-180 degrees).

The wettability alteration simulation can be a slow, dynamic process that occurs over small discrete time intervals. At any time during a displacement simulation, each surface element is tested to determine whether an alteration to, e.g., the contact angle occurred and determine the amount of the alteration. The history of the spatial expansion of the wettability alteration thus is captured as well. At any time increment, during the displacement simulation, the process measures the applied local pressure and compares that with the sum of the curvature based local pressure and the disjoining pressure. If film breakage occurs, the process modifies the local wettability classification. At any time increment, during the displacement simulation, the process measures the time that a second fluid, e.g., oil has been in contact with a surface element, and modifies the wettability classification correspondingly. The process continues with displacement simulation, e.g. relative permeability, by injection of a fluid or a capillary pressure increase of pressure during drainage. The process is performed where a final pressure represents reservoir pressure as described above or can be subdivided into several drainage pressure iterations where wettability alteration is carried out after each step followed by pressure ramp-up. The process 60 can thereafter allow the fluid phases to redistribute due to the modified surface wettability and repeat the process 60 until there is no or an insignificant (empirically or predetermined) amount of change in wettability.

With the process 60, the process provides 74 a numerical prediction of surface wettability alteration and resulting spatial distribution of wettability in the form of the calculated contact angle at each surface location. In process 60 a discrete surface element and one or more fluid elements are in communication, enabling local wettability determinations to depend on the local properties of mineral type, fluid properties, fluid composition (e.g. presence of asphaltenes), capillary pressure, and disjoining pressure. The slow dynamic wettability alteration allows non-wetting fluid to intrude into very small pores, because the wettability can be changed in such a way that capillary pressure does not need to be overcome.

In extensions, it is possible to use the method iteratively where wettability alteration is performed followed by fluid phase redistribution, with the process 60 being repeated until the system 10 converges (as measured by further repetitions not significantly changing the results (e.g., contact angles). Thus the process 60 could reference an established threshold value that provides an amount by which a contact angle would need to vary to otherwise halt further iterations of wettability alternation simulations.

The process 60 could also be used within a relative permeability simulation to predict, for example, wettability alteration that occurs during a physical relative permeability lab experiment (these can take months so some further alteration of wettability is possible even if a wettability restoration protocol was performed).

Achieving a force balance is the basic mechanism that defines a qualification rule for a wettability alteration. The qualification rule for a wettability alteration involves three forces:

(1) Capillary pressure ($P_C$), i.e., the pressure difference of non-wetting (oil) and wetting (water) fluid. It can come from boundary conditions directly, e.g. inlet Pressure of oil–outlet pressure of water ($P_{inlet\ oil}$–$P_{out\ water}$), but other test methods may also lead to a distribution of oil and water resulting in a capillary pressure, e.g. a relative permeability test.

(2) Curvature-based pressure ($P_V$), i.e., the pressure caused by a solid geometry forcing the shape of the oil/water interface into the shape of the geometry (i.e., the shape of rock surfaces/pores, etc. The curvature is calculated using geometric algorithm which are commonly available in various software libraries such as the VTK (Visualization Toolkit) mentioned above.

(3) Disjoining pressure ($P_D$), i.e., the pressure that prevents the film from rupturing, i.e., when the pressure applied to the film exceeds the maximum disjoining pressure, the film will rupture.

As explain in (3) above, the force balance requirement for film rupture can be expressed as:

($P_P > P_V + P_D$) or the capillary pressure is greater than the curvature based pressure plus the disjoining pressure or ($P_P - P_V > P_D$) or the capillary pressure minus the curvature based pressure is greater than the disjoining pressure.

Figure 4:
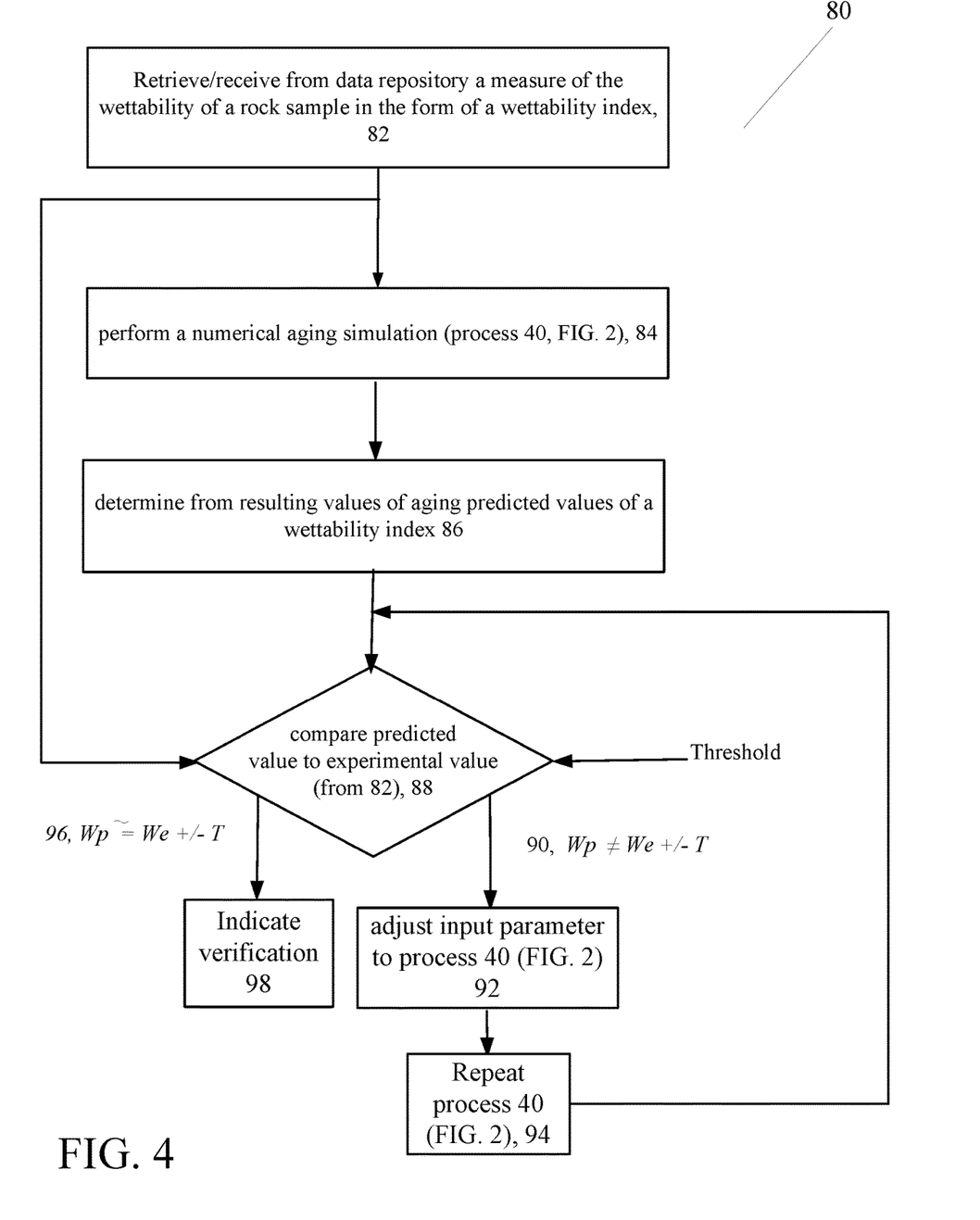
FIG. 4 depicts a flow chart showing operations validating/calibrating wettability alteration simulations.

Wettability Index Simulation:

Referring to FIG. 4, a verification process 80 is shown. The verification process provides a verification of the wettability calculation of FIG. 2, by use 82 of a measure of the wettability of a rock sample in the form of a wettability index, such as Amott index and USBM method (United States Bureau of Mines) index that are experimentally determined We. These values are used to verify and/or calibrate the predicted wettability distribution resulting from the numerical aging process 40 of FIG. 2. The Amott test is a well-known empirical wettability measurement for reservoir cores in petroleum engineering that combines two spontaneous imbibition measurements and two forced displacement measurements and defines two different indices, the Amott water index and the Amott oil index obtained from core analysis experiments.

The wettability index simulation process 80 performs 84 a numerical aging simulation based on estimated input parameters (see above) to provide simulation results. The process uses the simulation results to determine 86 predicted values of the wettability index Wp. The wettability index simulation process 80 compares 88 the predicted values to experimentally measured values We (from 82) and when the values do not match 90, Wp≠We±T sufficiently within a user defined tolerance T. The user defined tolerance on the match can be empirically or numerically determined based on tolerances of attributed to the experimental determination of the wettability index and/or tolerances on characteristics used in determining predictions, etc.

Thereafter, the process 80 iteratively modifies 92 one or more of the input parameter values to the numerical aging simulation process 40, and repeats 94 the numerical aging simulation process 40 until the values from the numerical aging simulation 40 agree 96 (Wp≅We±T) with those from the experimental values indicating verification 98.

As discussed above for FIG. 1, the parameter values are one or more grain surface properties 33a' obtained by engine 33a that assigns mineral types to the grains and determines the surface properties for each of those mineral types, parameters such as fluid properties 33b, e.g., fluid density and viscosity of each expected fluid and fluid-fluid interfacial tension properties, chemical composition data of the fluids and affinity data of the fluid components for the particular mineral surfaces and the disjoining pressure for each mineral type. Iterative modification is accomplished by the system 10 incrementing one or more of the parameter values by a defined incremental value. Both the parameter value that is incremented and the incremental value amount can be system determined or user determined.

Figures 5, 5A:
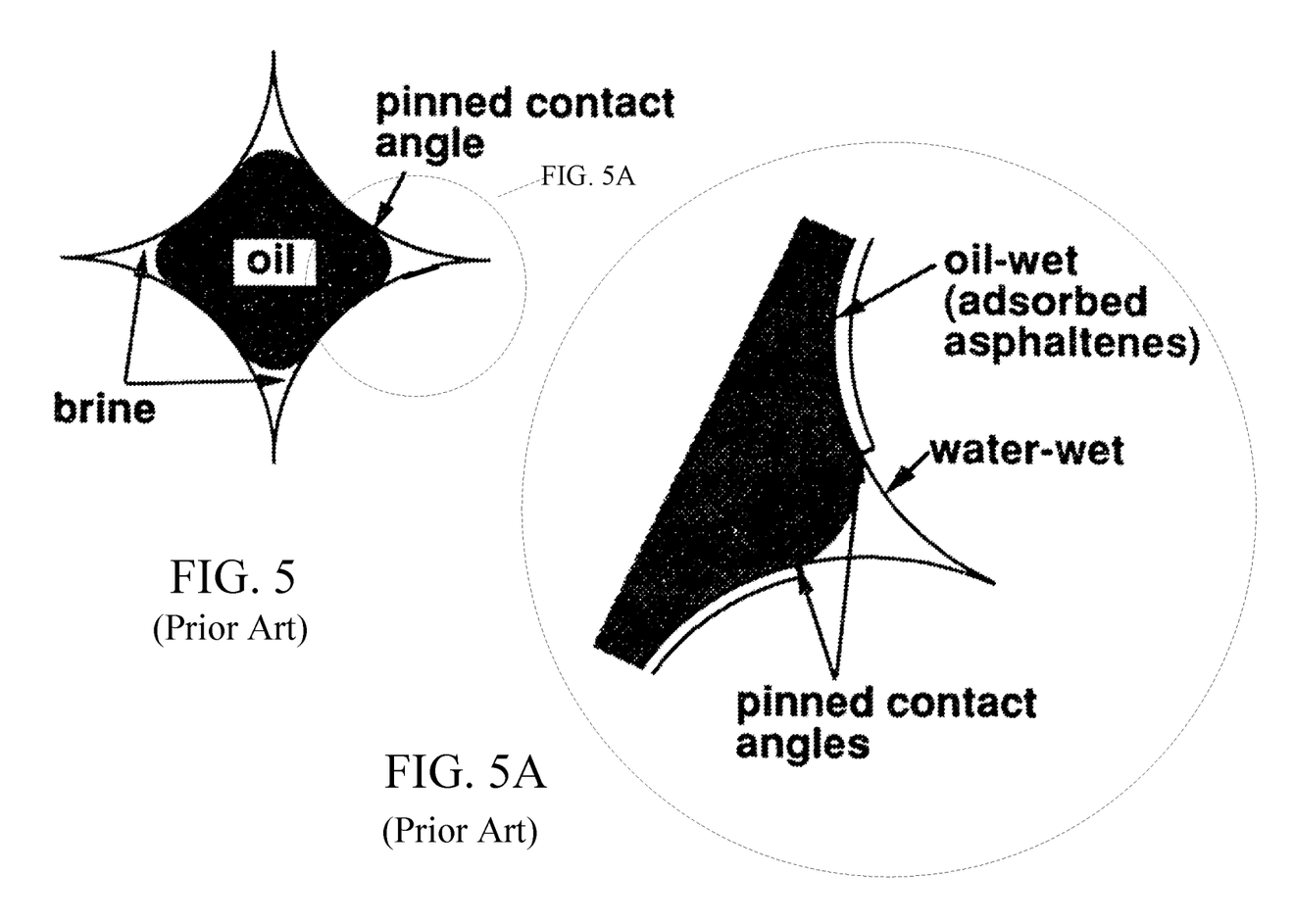
FIGS. 5, 5A depicts a prior art diagram of a pore in a rock sample showing pinned angles.

Referring to FIGS. 5 and 5A, these prior art figures depict conventional understandings of oil blob and brine providing pinned contact angles conventions for an illustrative rock sample portion. (Taken from A Pore-Level Scenario for the Development of Mixed-Wettability in Oil Reservoirs, by A. R. Kovscek et al DOE/BC-9200106 Distribution DE92 00162 September 1992 prepared for U.S. Department of Energy.)

Embodiments of the subject matter and the functional operations described in this specification can be implemented in digital electronic circuitry, tangibly-embodied computer software or firmware, computer hardware (including the structures disclosed in this specification and their structural equivalents), or in combinations of one or more of them. Embodiments of the subject matter described in this specification can be implemented as one or more computer programs (i.e., one or more modules of computer program instructions encoded on a tangible non-transitory program carrier for execution by, or to control the operation of, data processing apparatus). The computer storage medium can be a machine-readable storage device, a machine-readable storage substrate, a random or serial access memory device, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document, in a single file dedicated to the program in question, or in multiple coordinated files (e.g., files that store one or more modules, sub-programs, or portions of code)). A computer program can be deployed so that the program is executed on one computer or on multiple computers that are located at one site or distributed across multiple sites and interconnected by a data communication network.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data (e.g., magnetic, magneto-optical disks, or optical disks), however, a computer need not have such devices.

Computer-readable media suitable for storing computer program instructions and data include all forms of non-volatile memory on media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

What is claimed is:

1. A computer implemented method for simulating aging and a wettability alteration of a physical rock sample in the presence of at least two fluids including water and oil, with the method comprising, comprises:
    retrieving by a computing system a representation of a physical rock sample, the representation including chemical composition, pore space, and grain space data corresponding to the physical rock sample;
    iteratively simulating by the computing system aging and wettability alteration fora surface location in the pore space of the representation of the physical rock sample;
    calculating by the computing system, a change in a local curvature for the surface location in the pore space of the representation of the physical rock sample from a prior iteration of the wettability alteration, with calculating by the computing system, the change in local curvature comprising:
    calculating by the computing system, local capillary pressure and local disjoining pressure of the surface location in the pore space; and the method further comprises:
    determining from the calculated change in local curvature whether water-oil film breakage will occur;
    for some of the surface locations, determine whether water-oil film breakage will occur by comparing the capillary pressure to the sum of local curvature-based pressure and local disjoining pressure; and
    for at least some of the surface locations with water-oil film breakage, determine the degree of wettability alteration based on local surface properties, local fluid chemical composition, and aging;
    determining by the computer system a modified surface wettability of the surface location corresponding to the representation of the physical rock based on the change in the calculated local curvature; and
    verifying by the computer system a degree of aging in relation to an experimental value of aging of the physical rock sample, and terminating the iterative simulating, upon verification of the aging.

2. The method of claim 1 further comprises:
    assigning input parameters needed for wettability simulation to the computer simulation environment.

3. The method of claim 1 wherein the representation of the rock sample is modeled as a triangulated mesh and fluid is represented by voxels with voxels assigned attributes.

4. The method of claim 3 wherein voxels are cut to conform the fluid to the triangulated mesh.

5. The method of claim 1 further comprises:
    performing a drainage simulation to establish a fluid phase distribution according to user-specified conditions.

6. The method of claim 5 wherein the user-specified conditions are selected from the group consisting of representative laboratory and reservoir conditions.

7. The method of claim 6 wherein performing drainage simulation further comprises:
    simulating drainage using a fluid computational technique to establish fluid phase distribution for the user-specified conditions through the rock sample representation.

8. The method of claim 5 wherein performing drainage simulation further comprises:
    calculating the change in local curvature at each surface in the rock sample representation; and
    applying results of the change in the local curvature calculation to calculate the local capillary pressure at each surface location.

9. The method of claim 1 wherein after performing an iteration of determining the numerical representation of wettability alteration, the method further comprises:
    allowing the at least two fluids to redistribute due to the modified surface wettability.

10. The method of claim 1 wherein the method provides a numerical prediction of surface wettability alteration and resulting spatial distribution of wettability in the form of the calculated contact angle at each surface location.

11. The method of claim 1 wherein a discrete surface element and one or more fluid elements are in communication, and local wettability determinations are made that depend on the local properties of mineral type, fluid properties, fluid composition, capillary pressure, and disjoining pressure; and wherein wettability alteration is iteratively performed followed by fluid phase redistribution, with the wettability alteration repeated until the computing system detects a convergence measured by a subsequent repetition not significantly changing values of determined local curvature.

12. A computer system comprises:
    one or more processor devices;
    memory coupled to the one or more processor devices;
    storage storing executable computer instructions to simulate aging and a wettability alteration of a physical rock sample in the presence of at least two fluids that are oil and water, the instructions to configure the one or more processors to:
    retrieve a representation of a physical rock sample, the representation including chemical composition, pore space, and grain space data corresponding to the physical rock sample;
    iteratively simulate by the computing system aging and wettability alteration for a surface location in the pore space of the representation of the physical rock sample;

calculate a change in a local curvature for the surface location in the pore space of the representation of the physical rock sample from a prior iteration of the wettability alteration, with instructions to calculate the change in local curvature comprising:

calculate local capillary pressure and local disjoining pressure of the surface location in the pore space; and the method further comprises:

determine from the calculated change in local curvature whether water-oil film breakage will occur;

for some of the surface locations, determine whether water-oil film breakage will occur by comparing the capillary pressure to the sum of local curvature-based pressure and local disjoining pressure; and for at least some of the surface locations with water-oil film breakage, determine the degree of wettability alteration based on local surface properties, local fluid chemical composition, and aging;

determine a modified surface wettability of the surface location corresponding to the representation of the physical rock based on the change in the calculated local curvature; and verify a degree of aging in relation to an experimental value of aging of the physical rock sample, and terminate the iterative simulation, upon verification of the aging.

13. The computer system of claim 12 wherein instructions further configure the one or more processors to:

assign input parameters needed for wettability simulation to the computer simulation environment.

14. The computer system of claim 12 wherein the representation of the rock sample is modeled as a triangulated mesh and fluid is represented by voxels with voxels assigned attributes.

15. The computer system of claim 14 wherein voxels are cut to conform the fluid to the triangulated mesh.

16. The computer system of claim 12 further configure the one or more processors:

perform a drainage simulation to establish a fluid phase distribution according to user-specified conditions.

17. The computer system of claim 16 wherein the user-specified conditions are selected from the group consisting of representative laboratory and reservoir conditions.

18. The computer system of claim 17 wherein instructions to perform drainage simulation further configure the one or more processors:

simulate drainage using a fluid computational technique to establish fluid phase distribution for the user-specified conditions through the rock sample representation.

19. The computer system of claim 16 wherein instructions to perform drainage simulation further configure the one or more processors:

calculate the change in local curvature calculation at each surface in the rock sample representation; and apply results of the change in the local curvature calculation to calculate the local capillary pressure at each every surface location.

20. The computer system of claim 12 wherein after performing an iteration of determining the numerical representation of wettability alteration, the instructions further configure the one or more processors to:

allow the at least two fluids to redistribute due to the modified surface wettability.

21. The computer system of claim 12 wherein the computer system provides a numerical prediction of surface wettability alteration and resulting spatial distribution of wettability in the form of the calculated contact angle at each surface location.

22. The computer system of claim 12 wherein a discrete surface element and one or more fluid elements are in communication, and local wettability determinations are made that depend on the local properties of mineral type, fluid properties, fluid composition, capillary pressure, and disjoining pressure.

23. The computer system of claim 12 wherein wettability alteration is iteratively performed followed by fluid phase redistribution, with the wettability alteration repeated until the computer system detects a convergence measured by a subsequent repetition not significantly changing values of determined local curvature.

24. A computer program product tangibly stored on a computer readable non-transitory storage device that stores executable computer instructions to simulate aging and a wettability alteration of a physical rock sample in the presence of at least two fluids, the instructions for causing a computing system to:

retrieve a representation of a physical rock sample, the representation including chemical composition, pore space, and grain space data corresponding to the physical rock sample;

iteratively simulate by the computing system aging and wettability alteration for a surface location in the pore space of the representation of the physical rock sample;

calculate a change in a local curvature for the surface location in the pore space of the representation of the physical rock sample from a prior iteration of the wettability alteration, with instructions to calculate the change in local curvature comprising:

calculate local capillary pressure and local disjoining pressure of the surface location in the pore space; and the method further comprises:

determine from the calculated change in local curvature whether water-oil film breakage will occur;

for some of the surface locations, determine whether water-oil film breakage will occur by comparing the capillary pressure to the sum of local curvature-based pressure and local disjoining pressure; and for at least some of the surface locations with water-oil film breakage, determine the degree of wettability alteration based on local surface properties, local fluid chemical composition, and aging;

determine a modified surface wettability of the surface location corresponding to the representation of the physical rock based on the change in the calculated local curvature; and verify a degree of aging in relation to an experimental value of aging of the physical rock sample, and terminate the iterative simulation, upon verification of the aging.

25. The computer program product of claim 24 wherein instructions further comprises instructions to:

assign input parameters needed for wettability simulation to the computer simulation environment.

26. The computer program product of claim 24 wherein the representation of the rock sample is modeled as a triangulated mesh and fluid is represented by voxels with voxels assigned attributes.

27. The computer program product of claim 26 wherein voxels are cut to conform the fluid to the triangulated mesh.

28. The computer program product of claim 24 further comprises instructions to:

receive user specified conditions; and perform a drainage simulation to establish a fluid phase distribution according to the received user-specified conditions.

29. The computer program product of claim 28 wherein instructions to perform drainage simulation further comprises instructions to calculate the change in a local curvature calculation at each surface in the rock sample representation; and apply results of the change in the local curvature calculation to calculate the local capillary pressure at each surface location.

30. The computer program product of claim 24 wherein after performing an iteration of determining the numerical representation of wettability alteration, the computing system is further configured to:

allow the at least two fluids to redistribute due to the modified surface wettability.

31. The computer program product of claim 24 wherein the instructions cause the computing system to provide a numerical prediction of surface wettability alteration and resulting spatial distribution of wettability in the form of the calculated contact angle at each surface location.

32. The computer program product of claim 24 wherein a discrete surface element and one or more fluid elements are in communication, and local wettability determinations are made that depend on the local properties of mineral type, fluid properties, fluid composition, capillary pressure, and disjoining pressure.

33. The computer program product of claim 24 wherein wettability alteration is iteratively performed followed by fluid phase redistribution, with the wettability alteration repeated until the computing system detects a convergence measured by a subsequent repetition not significantly changing values of determined local curvature.

34. The method of claim 1 wherein wettability alteration is iteratively performed followed by fluid phase redistribution, with the wettability alteration repeated until the computing system detects a convergence measured by a subsequent repetition not significantly changing values of determined local curvature.

* * * * *